(12) United States Patent
Brown et al.

(10) Patent No.: US 10,604,802 B2
(45) Date of Patent: Mar. 31, 2020

(54) GENOME FRACTIONING

(71) Applicant: JumpCode Genomics, Inc., Carlsbad, CA (US)

(72) Inventors: Keith Brown, Carlsbad, CA (US); Peter Dansky, Solana Beach, CA (US)

(73) Assignee: JUMPCODE GENOMICS, INC., Carlsbad, CA (US)

( * ) Notice: Subject to any disclaimer, the term of this patent is extended or adjusted under 35 U.S.C. 154(b) by 3 days.

(21) Appl. No.: 15/116,404

(22) PCT Filed: Feb. 3, 2015

(86) PCT No.: PCT/US2015/014242
§ 371 (c)(1),
(2) Date: Aug. 3, 2016

(87) PCT Pub. No.: WO2015/119941
PCT Pub. Date: Aug. 13, 2015

(65) Prior Publication Data
US 2016/0348169 A1 Dec. 1, 2016

Related U.S. Application Data

(60) Provisional application No. 62/040,307, filed on Aug. 21, 214, provisional application No. 61/935,827, filed on Feb. 4, 2014.

(51) Int. Cl.
| | | |
|---|---|---|
| C12Q 1/68 | (2018.01) |
| C12N 15/10 | (2006.01) |
| C12Q 1/6874 | (2018.01) |
| C12Q 1/6811 | (2018.01) |

(52) U.S. Cl.
CPC ....... *C12Q 1/6874* (2013.01); *C12N 15/1093* (2013.01); *C12Q 1/68* (2013.01); *C12Q 1/6811* (2013.01)

(58) Field of Classification Search
None
See application file for complete search history.

(56) References Cited

U.S. PATENT DOCUMENTS

| | | |
|---|---|---|
| 2001/0031466 A1 | 10/2001 | Malek |
| 2005/0255089 A1 | 11/2005 | Chiorini et al. |
| 2006/0040297 A1 | 2/2006 | Leamon et al. |
| 2006/0252060 A1 | 11/2006 | Willis et al. |
| 2009/0036325 A1 | 2/2009 | McKernan et al. |
| 2009/0098548 A1 | 4/2009 | Ason et al. |
| 2010/0029498 A1 * | 2/2010 | Gnirke ............... C12Q 1/6869 506/9 |
| 2010/0287628 A1 | 11/2010 | Ostertag et al. |
| 2012/0252015 A1 | 10/2012 | Hindson et al. |
| 2012/0258892 A1 | 10/2012 | Wang |
| 2013/0315886 A1 | 11/2013 | Gage et al. |
| 2014/0357523 A1 | 12/2014 | Zeiner et al. |
| 2015/0159174 A1 | 6/2015 | Frendewey et al. |
| 2016/0376663 A1 | 12/2016 | Brown |

FOREIGN PATENT DOCUMENTS

| | | | |
|---|---|---|---|
| CN | 102439177 A | 5/2012 | |
| JP | 2003508082 A | 3/2003 | |
| WO | WO-9916908 A2 | 4/1999 | |
| WO | WO-2008134596 A2 | 11/2008 | |
| WO | WO-2012048113 A2 | 4/2012 | |
| WO | WO-2012061832 A1 | 5/2012 | |
| WO | WO-2013176772 A1 * | 11/2013 | ........... C12N 15/102 |
| WO | WO-2013191775 A2 * | 12/2013 | ........... C12Q 1/6806 |
| WO | WO-2015002780 A1 | 1/2015 | |
| WO | WO-2015131101 A1 | 9/2015 | |
| WO | WO-2017015075 A1 | 1/2017 | |

OTHER PUBLICATIONS

Jinek, Martin, et al. "A programmable dual-RNA—guided DNA endonuclease in adaptive bacterial immunity." science(2012): 1225829; published Jun. 28, 2012; 8 pages (Year: 2012).*
Jinek supp (Year: 2012).*
Shagina, Irina, et al. "Normalization of genomic DNA using duplex-specific nuclease." Biotechniques 48.6 (2010): 455-459. (Year: 2010).*
Gomaa, Ahmed A., et al. "Programmable removal of bacterial strains by use of genome-targeting CRISPR-Cas systems." MBio 5.1 (2014): e00928-13. (Year: 2014).*
Brouns, SJ Molecular biology. A Swiss army knife of immunity. Science 337(6069)808-9 (Aug. 17, 2012). -
Carpenter, et al. Pulling out the 1%: Whole-Genome Capture for the Targeted Enrichment of Ancient DNA Sequencing Libraries. The American Journal of Human Genetics 93, 852-864, 2013.
Deltcheva, et al. CRISPR RNA maturation by trans-encoded small RNA and host factor RNase III. Nature. Mar. 31, 2011;471(7340):602-7. doi: 10.1038/nature09886.
Dolinsek, et al. Depletion of unwanted nucleic acid templates by selective cleavage: LNAzymes, catalytically active oligonucleotides containing locked nucleic acids, open a new window for detecting rare microbial community members. App. Environ Microbiol 79(5); 1534-1544 (Mar. 2013).
Gao, X et al. In vivo cancer targeting and imaging with semiconductor quantum dots, Nature Biotechnology, 22(8);969-976 (Jul. 18, 2004).
International Application No. PCT/US2015/014242 International Preliminary Report on Patentability dated Aug. 9, 2016.

(Continued)

*Primary Examiner* — Tracy Vivlemore
*Assistant Examiner* — Sahana S Kaup
(74) *Attorney, Agent, or Firm* — Wilson Sonsini Goodrich & Rosati

(57) ABSTRACT

Disclosed herein are compositions and methods related to the elimination of molecules of a selected sequence from a nucleic acid sample or from an sequence dataset resulting from the sequencing of a sample, for example to exclude such molecules from downstream analysis or sequencing, or to exclude such sequences from a downstream data set.

17 Claims, 7 Drawing Sheets

(56) References Cited

OTHER PUBLICATIONS

International Application No. PCT/US2015/018115 International Preliminary Report on Patentability dated Aug. 30, 2016.
International Application No. PCT/US2015/018115 International Search Report and Written Opinion dated May 29, 2015.
International Application No. PCT/US2015/8014242 International Search Report and Written Opinion dated Jul. 30, 2015.
Jiang, W. et al. Demonstration of CRISPR/Cas9/sgRNA-mediated targeted gene modification in *Arabidopsis*, tobacco, sorghum and rice. Nucleic Acids Res. (Nov. 2013), 41(20):e188.
Jinek et al. A programmable dual-RNA-guided DNA endonuclease in adaptive bacterial immunity. Science 337:816-821 (2012).
Kolpashchikov, D. An Elegant Biosensor Molecular Beacon probe: Challenges and Recent Solutions, Scientifica 2012;1-17 (Dec. 3, 2012) Article ID 928783.
Laurent, St G. III et al. A LINE-1 component to human aging: do LINE elements exact a longevity cost for evolutionary advantage? Mechanisms of Ageing and Development, 131(5); 299-305 (May 1, 2010).
Lee, E. et al. Landscape of Somatic Retrotransposition in Human Cancers, Science 337(6097); 967-971 (Jun. 28, 2012) Supplement.
Li, W. et al. Activation of transposable elements during aging and neuronal decline in *Drosophila*, Nature Neuroscience 16(5);529-531 (Apr. 7, 2013).
Soriano, V. et al. Hepatitis C virus-RNA clearance in HIV-coinfected patients with chronic hepatitis C treated with pegylated interferon plus ribavirin. Antiviral Therapy, 9;505-509 (2004).
Terns, et al. CRISPR-based adaptive immune systems. Curr Opin Microbiol. Jun. 2011;14(3):321-7.
Vlad, SC et al. Protective effects of NSAIDs on the development of Alzheimer disease.Neurology, 70(19); 1672-1677 (May 6, 2008).
Adiconis, Xian et al. Comparative analysis of RNA sequencing methods for degraded or low-input samples, Nature Methods, 10(7):623-629 (May 19, 2013).
Co-pending U.S. Appl. No. 15/553,495, filed Aug. 24, 2017.
European Application No. 15746731.7 Search Report dated Sep. 5, 2017.
Green, S.J. et al. Suicide Polymerase Endonuclease Restriction, a novel technique for enhancing PCR amplification of minor DNA templates, Applied and Environmental Microbiology, 71(8):4721-4727 (Aug. 1, 2005).
International Application No. PCT/US2016/019609 International Preliminary Report on Patentability dated Aug. 29, 2017.
International Application No. PCT/US2017/017530 International Search Report and Written Opinion dated May 15, 2017.
Zhang, F. et al. CRISPR/Cas9 for genome editing: Progress, Implications and challenges. Human Molecular Genetics 23(R1):R40-R46 (Mar. 20, 2014).
European Patent Application No. 15754498.2 European Search Report dated Nov. 27, 2017.
Iskow, Rebecca C. et al. Natural Mutagenesis of Human Genomes by Endogenous Retrotransposons, CELL 141(1):1253-1261 (Jun. 1, 2010).
Shukla, Ruchi et al. Endogenous Retrotransposition Activates Oncogenic Pathways in Hepatocellular Carcinoma, CELL 153(1):101-111 (Mar. 1, 2013).
International Application No. PCT/US2017/017530 International Preliminary Report on Patentability dated Aug. 23, 2018.
Kantarjian, H.M. et al. Dose escalation of imatinib mesylate can overcome resistance to standard-dose therapy in patients with chronic myelogenous leukemia. BLOOD, 101(2):473- 475 (Jan. 15, 2003).
Lerat, E. et al. Influence of the transposable element neighborhood on human gene expression in normal and tumor tissues. Gene 396:303-311 (2007).
U.S. Appl. No. 15/121,725 Final Office Action dated Sep. 6, 2018.
U.S. Appl. No. 15/121,725 Non-Final Office Action dated Feb. 9, 2018.

\* cited by examiner dsDNA produced and cleaved from array.

T7 polymerase creates guide RNAs from dsDNA template molecules

Guide RNAs produced

Target site

Tracr RNA includes palindromic sequence for hairpin

GENOME FRACTIONING

RELATED APPLICATIONS

The present application claims priority to U.S. Provisional Application Ser. No. 61/935,827, filed on Feb. 4, 2014, the contents of which are hereby explicitly incorporated by reference in their entirety, and also claims priority to U.S. Provisional Application Ser. No. 62/040,307, filed Aug. 21, 2014, the contents of which are hereby also explicitly incorporated by reference in their entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

Some embodiments relate to methods of removing a nontarget sequence from a nucleic acid library. Some aspects of the se embodiments relate to methods of removing a nontarget sequence from a nucleic acid library comprising providing a nucleic acid library, comprising a plurality of nucleic acid molecules, wherein each nucleic acid molecule comprises a first adapter region, a target sequence region, and a second adapter region, and wherein at least one of said nucleic acid molecules comprises target sequence that comprises said nontarget sequence; contacting the nucleic acid library with a nucleic acid modifying moiety that modifies said nontarget sequence; and sequencing said nucleic acid library using a sequencing approach that requires a first universal adapter region and a second universal adapter region spanning a target sequence region. In some aspects, the sequencing comprises next-generation sequencing. In some aspects, the sequencing comprises amplifying said target sequence using a first primer that anneals to said first universal region and a second primer that anneals to said second universal region. In some aspects the first adapter region is a universal adapter region, such as an adapter region compatible with a 'next generation' sequencing platform such as a sequencing by synthesis platform. In some aspects, the contacting interferes with said sequencing. In some aspects, the contacting comprises cleaving said target sequence such that said first universal region and said second universal region are not physically joined through said target region. In some aspects, the contacting comprises binding said nontarget sequence. In some aspects, the contacting comprises methylating said specific nucleic acid sequence. In some aspects, the contacting comprises cleaving said specific nucleic acid sequence. In some aspects, the nucleic acid modifying moiety comprises a restriction endonuclease. In some aspects, the nucleic acid modifying moiety comprises a methyltransferase. In some aspects, the nucleic acid modifying moiety comprises an enzyme having base excision activity. In some aspects, the nucleic acid modifying moiety comprises a guide RNA molecule. In some aspects, the nucleic acid modifying moiety comprises a guide RNA molecule comprising a hairpin. In some aspects, the nucleic acid modifying moiety comprises a guide RNA molecule comprising a tracr hairpin. In some aspects, the nucleic acid modifying moiety comprises a guide RNA molecule comprises a protospacer adjacent motif sequence. In some aspects, the nucleic acid modifying moiety comprises a guide RNA molecule comprises a protospacer adjacent motif sequence comprising the sequence NGG. In some aspects, the nucleic acid modifying moiety comprises a guide RNA molecule comprises a protospacer adjacent motif sequence comprising the sequence NGGNG. In some aspects, the nucleic acid modifying moiety comprises a guide RNA molecule-directed endonuclease. In some aspects, the guide RNA molecule-directed endonuclease comprises a Cas9 endonuclease. In some aspects, the nontarget sequence comprises low-information content sequence. In some aspects, the nontarget sequence comprises repetitive sequence. In some aspects, the nontarget sequence comprises Alu repeat sequence. In some aspects, the nontarget sequence comprises SINE element sequence. In some aspects, the nontarget sequence comprises LINE sequence. In some aspects, the nontarget sequence comprises retroviral sequence. In some aspects, the nontarget sequence comprises DNA encoding ribosomal RNA. In some aspects, the nontarget sequence comprises telomeric sequence. In some aspects, the nontarget sequence comprises subtelomeric sequence. In some aspects, the nontarget sequence comprises centromeric sequence. In some aspects, the nontarget sequence comprises a single repeat. In some aspects, the nontarget sequence comprises nonrepetative sequence. In some aspects, the nontarget sequence comprises sequence encoding a protein. In some aspects, the nontarget sequence comprises at least one of a repetitive sequence, an Alu repeat sequence, a SINE element sequence, LINE sequence, DNA encoding ribosomal RNA, telomeric sequence, subtelomeric sequence, centromeric sequence, and a single repeat. In some aspects, the nontarget sequence comprises at least 10% of said nucleic acid library target sequence. In some aspects, the nontarget sequence comprises at least 20% of said nucleic acid library target sequence. In some aspects, the nontarget sequence comprises at least 30% of said nucleic acid library target sequence. In some aspects, the nontarget sequence comprises at least 40% of said nucleic acid library target sequence. In some aspects, the nontarget sequence comprises at least 50% of said nucleic acid library target sequence. In some aspects, the nontarget sequence comprises at least 60% of said nucleic acid library target sequence. In some aspects, the nontarget sequence comprises about ⅔ of said nucleic acid library target sequence. In some aspects, at least one nucleic acid of said library is bound to a next generation sequencing platform. In some aspects, the NGS sequencing platform comprises at least one of a solid platform, a bead, a lipid or oil droplet, and a well surface. In some aspects, the sequencing occurs in a first sequencing time duration that is reduced relative to a second sequencing time duration of said nucleic acid library in the absence of said contacting. In some aspects, the first sequencing time duration is less than 90% that of said second sequencing time duration. In some aspects, the first sequencing time duration is less than 80% that of said second sequencing time duration. In some aspects, the first sequencing time duration is less than 70% that of said second sequencing time duration. In some aspects, the first sequencing time duration is less than 60% that of said second sequencing time duration. In some aspects, the first sequencing time duration is less than 50% that of said second sequencing time duration. In some aspects, the first sequencing time duration is less than 40% that of said second sequencing time duration. In some aspects, the first sequencing time duration is less than 33% that of said second sequencing time duration.

Some embodiments relate to compositions. Some embodiments relate to compositions comprising: a nucleic acid library comprising a plurality of nucleic acid molecules; and a nontarget nucleic acid binding moiety, wherein each nucleic acid molecule comprises a first universal sequence, a target sequence, and a second universal sequence, and wherein at least one target sequence of at least one nucleic acid molecule of said nucleic acid library comprises a nontarget sequence. In some aspects, the nontarget nucleic acid binding moiety comprises a first guide RNA. In some aspects, the first guide RNA comprises a protospacer adjacent motif sequence. In some aspects, the protospacer adjacent motif sequence comprises NGG. In some aspects, the protospacer adjacent motif sequence comprises NGGNG. In some aspects, the first guide RNA is hybridized to said nontarget sequence. In some aspects, the first guide RNA binds at least one substrate sequence selected from the list consisting of low-information content sequence, repetitive sequence, Alu repeat sequence, SINE element sequence, LINE sequence, DNA encoding ribosomal RNA, retroviral sequence, telomeric sequence, subtelomeric sequence, centromeric sequence, nonrepetative sequence, and sequence encoding a protein. In some aspects, the nontarget sequence comprises at least one sequence selected from the list consisting of low-information content sequence, repetitive sequence, Alu repeat sequence, SINE element sequence, LINE sequence, DNA encoding ribosomal RNA, retroviral sequence, telomeric sequence, subtelomeric sequence, centromeric sequence, nonrepetative sequence, and sequence encoding a protein. In some aspects, the nontarget nucleic acid binding moiety comprises a first guide RNA and a second guide RNA, wherein said second guide RNA binds at least one substrate that is not identical to a substrate bound by said first guide RNA. In some aspects, the composition comprises a DNA endonuclease. In some aspects, the DNA endonuclease comprises at least one endonuclease selected from the list consisting of a Zinc Finger Nuclease (ZFN), a Transcription activator like effector nuclease and a Clustered Regulatory Interspaced Short palindromic Repeat/Cas based RNA guided DNA nuclease. In some aspects, the DNA endonuclease binds said guide RNA. In some aspects, the DNA endonuclease is Cas9. In some aspects, the nontarget nucleic acid binding moiety comprises a restriction endonuclease.

Some embodiments relate to a nucleic acid molecule, such as a construct. Some embodiments relate to a nucleic acid molecule comprising a transcription promoter and a template, said template comprising a first region directing transcription of a tag sequence, and a second region directing transcription of a recognition sequence. In some aspects, the transcription promoter is a viral promoter. In some aspects, the transcription promoter is a phage T7 promoter. In some aspects, the first region directs transcription of a stem loop. In some aspects, the first region directs transcription of a tracr stem loop. In some aspects, the first region directs transcription of a tag that binds an endonuclease. In some aspects, the first region directs transcription of a tag that binds a Cas9 endonuclease. In some aspects, the first region and said second region are separated by a cloning site. In some aspects, the first region comprises a protospacer adjacent motif sequence. In some aspects, the protospacer adjacent motif comprises the sequence NGG. In some aspects, the protospacer adjacent motif comprises the sequence NGGNG.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

Figure 1A:
FIG. 1A depicts a double stranded DNA template from which a guide RNA molecule may be synthesized.
Figure 1B:
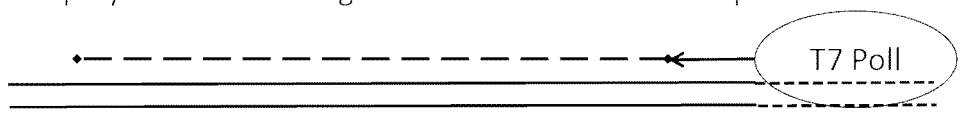
FIG. 1B depicts T7 RNA polymerase performing DNA directed RNA synthesis (transcription) of a guide RNA molecule.
Figure 1C:
FIG. 1C depicts a guide RNA molecule. The guide RNA molecule comprises a target site that binds to a sequence to be selectively eliminated from a sequencing library, and a tracr RNA hairpin sequence comprising palindromic arm sequence and a linking loop sequence.
Figure 1D:
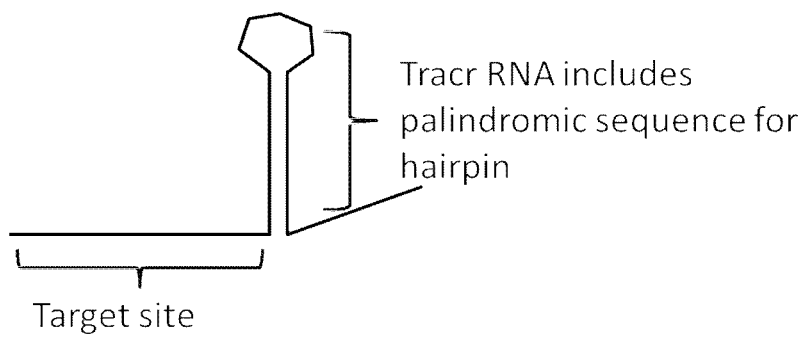
FIG. 1D depicts a cartoon drawing of a guide RNA molecule with the palindromic arms of its tracr RNA hairpin properly annealed.
Figure 2A:
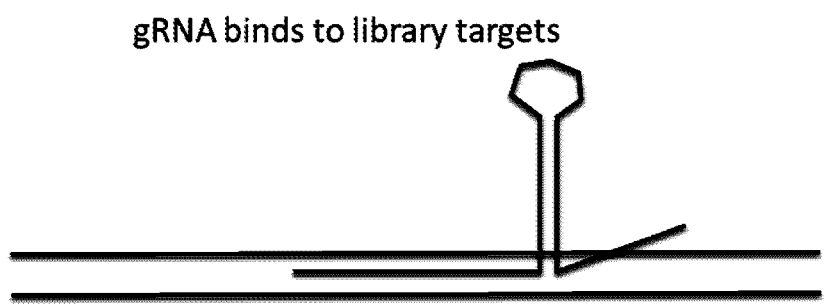
FIG. 2A depicts a guide RNA bound to a sequence to be selectively eliminated from a sequencing library.
Figure 2B:
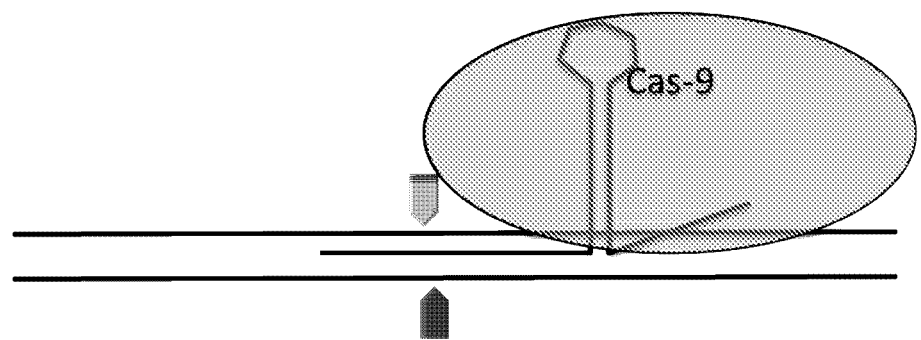
FIG. 2B depicts a Cas9 DNA endonuclease bound to a guide RNA/library complex. The Cas9 cleaves the library molecule in a manner directed by guide RNA binding.

Next Generation DNA sequencing technologies (NGS) have the potential to revolutionize the field of medical genetics. With these massively parallel sequencing systems, the cost of sequencing a human genome has dropped dramatically and may continue to do so. The use of clinical whole genome sequencing is a near term reality. The problem has now shifted toward understanding the information these NGS systems produce.

About ⅔ of the human genome consists of repetitive elements such as mobile elements (including Alus, LINE and SINE), introns, viral insertions, centromeres and telomeres. Though these elements have been associated with disease, our ability to map short reads to a specific locus within these sequence types is cumbersome and prone to errors. When mapping is successful, interpretation of the variation in these regions becomes the problem when trying to provide a clinical diagnosis. Regulatory and advisory bodies have implemented applications like targeted sequencing and exome sequencing for certain applications in the clinic because these regions are "interpretable" to some extent. The technologies used for targeted sequencing today have their own set of problems including an extensive dropout rate and the inability to detect complex variation.

Similarly, in transcriptome nucleic acid libraries, ribosomal RNA, viral, or other high copy accumulating sequences can dominate the nucleic acid pool and complicate the collection of information related to transcripts accumulating at low levels.

Described herein are targeted sequencing techniques called genome fractioning that can focus on high information content regions of a genome, such as the genes and genomic loci on a region where a definitive diagnosis can be made, without limiting to a single locus or a single target amplicon. In some embodiments these targeted sequencing techniques work by removing regions of low information content or repetitive sequence, for example, from the set of nucleic acid molecules available for sequencing. As a result, sequencing reactions can be run much more quickly, with fewer reagents, to generate less sequencing data, which can in turn be assembled into contigs more quickly and which occupy less data storage space—and without any substantial loss in the amount of high-information content sequence to be obtained through the reaction.

Methods of genome sequencing that remove all or a fraction of troublesome and/or unwanted regions of the genome for clinical use are described. Such methods will, in some instances, be comprehensive across all regions of clinical interest while avoiding those that are unwanted. In contrast to targeted sequencing strategies which require the regions of interest to be selected and amplified, genome fractioning focuses on removing the unwanted sequences, (e.g. repetitive sequences) from an NGS DNA library. The sequences removed may include, but are not limited to, DNA (e.g. genomic DNA) molecules that are unwanted in results and DNA converted from an RNA sample input (e.g. via reverse-transcription), or libraries thereof. In some cases, ribosomal RNA, GLOBIN genes, and/or overexpressed transcripts, which may minimize the cost effective use of massively parallel sequencing, are removed.

Disclosed herein are methods for using genome editing techniques which can be used to alter genomes in cells and animal models. These techniques, including Zinc Finger Nucleases (ZFN), Transcription activator like effector nucleases and Clustered Regulatory Interspaced Short palindromic Repeat/Cas based RNA guided DNA nuclease (CRISPR/Cas9) allow for sequence specific degradation of double stranded DNA. To date, none of these techniques have been used for genome fractioning for NGS sample prep. These techniques can be used to, for example, remove unwanted sequences from an NGS library.

The ability to target sequence specific locations for double stranded DNA cuts makes these genome editing tools compatible with Genome Fractioning. The NGS protocols require the production of DNA libraries. Numerous library generation methods have been described. The result of DNA library preparation is a pool of unknown sample derived sequences of about, for example, 100-1000 bp in length flanked by synthetic sequences of known configuration. The known sequences are used for other aspects of NGS sequencing including cluster generation and priming sites for sequencing by synthesis reactions. The generation of these NGS libraries may involve all, substantially all, or a selected fraction of the sequences in the sample genome from which it was generated. Genome Fractioning can be applied post library generation to remove undesired sequences from the DNA library prior to sequencing. This can allow for a complexity reduction that minimizes mapping and alignment errors and, in the case of the human genome, allows one to focus reagent and computing time only on the ⅓ of the human genome that is assayable as DNA today for clinical purposes. The DNA molecules with undesired sequence can be cut, which may render them inactive for downstream processing steps such as PCR, thereby effectively removing the DNA comprising undesired sequences from analysis.

In some cases an NGS sequencing library is provided for use with the methods and compositions disclosed herein. Some NGS sequencing libraries comprise a plurality of nucleic acid molecules, each molecule comprising a first conserved region, a target region and a second conserved region, wherein the first conserved region comprises nucleic acid sequence that is added to facilitate NGS sequencing efforts, wherein the target region comprises nucleic acid sequence of a target sample, and wherein the second conserved region comprises nucleic acid sequence that is added to facilitate NGS sequencing efforts.

In some embodiments an NGS sequencing library is provided that comprises at least one constituent that is bound to an NGS sequencing platform such as a solid platform, a bead, a lipid or oil droplet, or a well surface. Alternately, in some embodiments an NGS sequencing library is provided wherein each constituent of the library remains in solution.

Alternately, in some cases the methods and compositions herein are applied to a nucleic acid population other than an NGS library.

A target sample from which target regions are generated comprises sequence of high information content and sequence of low information content in many cases. In some embodiments a target sample from which target regions are generated comprises non-repetitive sequence and repetitive sequence. In some embodiments a target sample from which target regions are generated comprises single-copy sequence and multi-copy sequence.

Provided herein are methods, compositions and kits related to the selective enrichment of high information content sequence or single-copy sequence. Also provided herein are methods for the selective exclusion from a sequencing reaction or from a sequence data set of low information content sequence, repetitive sequence, multi-copy sequence. In some embodiments, specific low-information content sequence, repetitive sequence, multi-copy sequence or sequence to be otherwise eliminated from a sample or from a sequencing dataset resulting from sequencing of that sample comprises sequence encoding ribosomal RNA (rRNA), sequence encoding globin proteins, sequencing encoding a transposon, sequence encoding retroviral sequence, sequence comprising telomere sequence, sequence comprising sub-telomeric repeats, sequence comprising centromeric sequence, sequence comprising intron sequence, sequence comprising Alu repeats, SINE repeats, LINE repeats, dinucleic acid repeats, trinucleic acid repeats, tetranucleic acid repeats, poly-A repeats, poly-T repeats, poly-C repeats, poly-G repeats, AT-rich sequence, or GC-rich sequence.

In some cases, specific low-information content sequence, repetitive sequence, or sequence to be otherwise eliminated from a sample or from a sequencing dataset resulting from sequencing of that sample comprises sequence reverse-transcribed from RNA encoding ribosomal RNA, RNA encoding globins, RNA encoding overexpressed transcripts, or RNA that is otherwise disproportionately present or redundantly present in a sample.

In some embodiments a specific low-information content sequence, repetitive sequence, or sequence to be otherwise eliminated from a sample or from a sequencing dataset resulting from sequencing of that sample (such as one or more sequence from the list recited above) is targeted, for example using a moiety that specifically binds to the sequence. In some embodiments, a plurality of moieties comprises a first member that binds to a sequence to be eliminated from a sample or from a sequencing dataset resulting from sequencing of that sample, and a second member that binds to a second sequence to be eliminated from a sample or from a sequencing dataset resulting from sequencing of that sample. In some embodiments, a plurality of moieties includes members that bind to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the low-information content sequence, repetitive sequence, or sequence to be otherwise eliminated from a sample or from a sequencing dataset resulting from sequencing of that sample of a target sample.

In some embodiments, a plurality of moieties includes members that bind to 1%-100%, 2%-100%, 3%-100%, 4%-100%, 5%-100%, 6%-100%, 7%-100%, 8%-100%, 9% 100%, 10%-100%, 11%-100%, 12%-100%, 13%-100%, 14%-100%, 15%-100%, 16%-100%, 17%-100%, 18%-100%, 19%-100%, 20%-100%, 21%-100%, 22%-100%, 23%-100%, 24% -100%, 25%-100%, 26%-100%, 27%-100%, 28%-100%, 29%-100%, 30%-100%, 31%-100%, 32%-100%, 33%-100%, 34%-100%, 35%-100%, 36%-100%, 37%-100%, 38%-100%, 39% -100%, 40%-100%, 41%-100%, 42%-100%, 43%-100%, 44%-100%, 45%-100%, 46%-100%, 47%-100%, 48%-100%, 49%-100%, 50%-100%, 51%-100%, 52%-100%, 53%-100%, 54% -100%, 55%-100%, 56%-100%, 57%-100%, 58%-100%, 59%-100%, 60%-100%, 61%-100%, 62%-100%, 63%-100%, 64%-100%, 65%-100%, 66%-100%, 67%-100%, 68%-100%, 69% -100%, 70%-100%, 71%-100%, 72%-100%, 73%-100%, 74%-100%, 75%-100%, 76%-100%, 77%-100%, 78%-100%, 79%-100%, 80%-100%, 81%-100%, 82%-100%, 83%-100%, 84% -100%, 85%-100%, 86%-100%, 87%-100%, 88%-100%, 89%-100%, 90%-100%, 91%-100%, 92%-100%, 93%-100%, 94%-100%, 95%-100%, 96%-100%, 97%-100%, 98%-100%, 99% -100% or 100% of the low-information content sequence, repetitive sequence, or sequence to be otherwise eliminated from a sample (such as categories of sequence identified herein) or from a sequencing dataset resulting from sequencing of that sample of a target sample.

In some embodiments, a plurality of moieties includes members that bind to 1%, 1% -2%, 1%-3%, 1%-4%, 1%-5%, 1%-6%, 1%-7%, 1%-8%, 1%-9%, 1%-10%, 1%-11%, 1% -12%, 1%-13%, 1%-14%, 1%-15%, 1%-16%, 1%-17%, 1%-18%, 1%-19%, 1%-20%, 1% -21%, 1%-22%, 1%-23%, 1%-24%, 1%-25%, 1%-26%, 1%-27%, 1%-28%, 1%-29%, 1% -30%, 1%-31%, 1%-32%, 1%-33%, 1%-34%, 1%-35%, 1%-36%, 1%-37%, 1%-38%, 1% -39%, 1%-40%, 1%-41%, 1%-42%, 1%-43%, 1%-44%, 1%-45%, 1%-46%, 1%-47%, 1% -48%, 1%-49%, 1%-50%, 1%-51%, 1%-52%, 1%-53%, 1%-54%, 1%-55%, 1%-56%, 1% -57%, 1%-58%, 1%-59%, 1%-60%, 1%-61%, 1%-62%, 1%-63%, 1%-64%, 1%-65%, 1% -66%, 1%-67%, 1%-68%, 1%-69%, 1%-70%, 1%-71%, 1%-72%, 1%-73%, 1%-74%, 1% -75%, 1%-76%, 1%-77%, 1%-78%, 1%-79%, 1%-80%, 1%-81%, 1%-82%, 1%-83%, 1% -84%, 1%-85%, 1%-86%, 1%-87%, 1%-88%, 1%-89%, 1%-90%, 1%-91%, 1%-92%, 1% -93%, 1%-94%, 1%-95%, 1%-96%, 1%-97%, 1%-98%, 1%-99% or 100% of the low-information content sequence, repetitive sequence, or sequence to be otherwise eliminated from a sample (such as categories of sequence identified herein) or from a sequencing dataset resulting from sequencing of that sample of a target sample.

In some embodiments the low-information content sequence, repetitive sequence, or sequence to be otherwise eliminated from a sample or from a sequencing dataset resulting from sequencing of that sample of a target sample comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99% of the sequence in a target nucleic acid sample.

In some embodiments, the target sample is a human genomic DNA sample. In some embodiments, the low-information content sequence, repetitive sequence, or sequence to be otherwise eliminated from a sample or from a sequencing dataset resulting from sequencing of that sample of a target human genomic DNA sample comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or more than 70% of a sample. In some embodiments the low-information content sequence, repetitive sequence, or sequence to be otherwise eliminated from a sample or from a sequencing dataset resulting from sequencing of that sample of a target human genomic DNA sample comprises ⅔ or about ⅔ of a sample. In some embodiments the low-information content sequence, repetitive sequence, or sequence to be otherwise eliminated from a sample (such as sequence categories recited herein) or from a sequencing dataset resulting from sequencing of that sample of a target human genomic DNA sample comprises ⅔ of a sample.

In some embodiments a moiety that specifically binds to a specific low-information content sequence, repetitive sequence, or sequence to be otherwise eliminated from a sample or from a sequencing dataset resulting from sequencing of that sample comprises a restriction endonuclease, such as a specific endonuclease that binds and cleaves at a recognition site that is specific to low-information content sequence, repetitive sequence, or sequence to be otherwise eliminated from a sample or from a sequencing dataset resulting from sequencing of that sample. In some embodiments a population of moieties that specifically bind to a plurality of specific low-information content sequences, repetitive sequences, repetitive sequences or sequences to be otherwise eliminated from a sample or from a sequencing dataset resulting from sequencing of that sample comprises at least one restriction endonuclease, two restriction endonucleases or more than two restriction endonucleases.

In some embodiments a moiety that specifically binds to a specific low-information content sequence, repetitive sequence, or sequence to be otherwise eliminated from a sample or from a sequencing dataset resulting from sequencing of that sample comprises a guide RNA molecule. In some embodiments a population of moieties that specifically bind to a specific low-information content sequence, repetitive sequence, or sequence to be otherwise eliminated from a sample or from a sequencing dataset resulting from sequencing of that sample comprises a population of guide RNA molecules, such as a population of guide molecules that bind to at least one specific low-information content sequence, repetitive sequence, or sequence to be otherwise eliminated from a sample or from a sequencing dataset resulting from sequencing of that sample.

In some embodiments the guide RNA molecule interferes with sequencing directly, for example by binding the target sequence to prevent nucleic acid polymerization to occur across the bound sequence. In some embodiments the guide RNA molecule works in tandem with a RNA-DNA hybrid binding moiety such as a protein. In some embodiments the guide RNA molecule directs modification of member of the sequencing library to which it may bind, such as methylation, base excision, or cleavage, such that in some embodiments the member of the sequencing library to which it is bound becomes unsuitable for further sequencing reactions. In some embodiments, the guide RNA molecule directs endonucleolytic cleavage of the DNA molecule to which it is bound, for example by a protein having endonuclease activity such as Cas9 protein. Zinc Finger Nucleases (ZFN), Transcription activator like effector nucleases and Clustered Regulatory Interspaced Short palindromic Repeat/Cas based RNA guided DNA nuclease (CRISPR/Cas9), among others, are compatible with some embodiments of the disclosure herein.

A guide RNA molecule comprises sequence that base-pairs with target sequence that is to be removed from sequencing (non-target sequence within the target sequence region). In some embodiments the base-pairing is complete, while in some embodiments the base pairing is partial or comprises bases that are unpaired along with bases that are paired to non-target sequence.

A guide RNA may comprise a region or regions that form an RNA 'hairpin' structure. Such region or regions comprise partially or completely palindromic sequence, such that 5' and 3' ends of the region may hybridize to one another to form a double-strand 'stem' structure, which in some embodiments is capped by a non-palindromic loop tethering each of the single strands in the double strand loop to one another.

In some embodiments the Guide RNA comprises a stem loop such as a tracrRNA stem loop. A stem loop such as a tracrRNA stem loop may complex with or bind to a nucleic acid endonuclease such as Cas9 DNA endonuclease. Alternately, a stem loop may complex with an endonuclease other than Cas9 or with a nucleic acid modifying enzyme other than an endonuclease, such as a base excision enzyme, a methyltransferase, or an enzyme having other nucleic acid modifying activity that interferes with one or more DNA polymerase enzymes.

The tracrRNA/CRISPR/Endonuclease system was identified as an adaptive immune system in eubacterial and archaeal prokaryotes whereby cells gain resistance to repeated infection by a virus of a known sequence. See, for example, Deltcheva E, Chylinski K, Sharma C M, Gonzales K, Chao Y, Pirzada Z A et al. (2011) "CRISPR RNA maturation by trans-encoded small RNA and host factor RNase III" Nature 471 (7340): 602-7. doi:10.1038/nature09886. PMC 3070239. PMID 21455174; Terns M P, Terns R M (2011) "CRISPR-based adaptive immune systems" Curr Opin Microbiol 14 (3): 321-7. doi:10.1016/j.mib.2011.03.005. PMC 3119747. PMID 21531607; Jinek M, Chylinski K, Fonfara I, Hauer M, Doudna J A, Charpentier E (2012) "A Programmable Dual-RNA-Guided DNA Endonuclease in Adaptive Bacterial Immunity" Science 337 (6096): 816-21. doi:10.1126/science.1225829. PMID 22745249; and Brouns S J (2012) "A swiss army knife of immunity" Science 337 (6096): 808-9. doi:10.1126/science.1227253. PMID 22904002. The system has been adapted to direct targeted mutagenesis in eukaryotic cells. See, e.g., Wenzhi Jiang, Huanbin Zhou, Honghao Bi, Michael Fromm, Bing Yang, and Donald P. Weeks (2013) "Demonstration of CRISPR/Cas9/sgRNA-mediated targeted gene modification in *Arabidopsis*, tobacco, sorghum and rice" Nucleic Acids Res. November 2013; 41(20): e188, Published online Aug. 31, 2013. doi: 10.1093/nar/gkt780, and references therein.

As contemplated herein, guide RNA are used in some embodiments to provide sequence specificity to a DNA endonuclease such as a Cas9 endonuclease. In these embodiments a guide RNA comprises a hairpin structure that binds to or is bound by an endonuclease such as Cas9 (other endonucleases are contemplated as alternatives or additions in some embodiments), and a guide RNA further comprises a recognition sequence that binds to or specifically binds to or exclusively binds to a sequence that is to be removed from a sequencing library or a sequencing reaction. The length of the recognition sequence in a guide RNA may vary according to the degree of specificity desired in the sequence elimination process. Short recognition sequences, comprising frequently occurring sequence in the sample or comprising differentially abundant sequence (abundance of AT in an AT-rich genome sample or abundance of GC in a GC-rich genome sample) are likely to identify a relatively large number of sites and therefore to direct frequent nucleic acid modification such as endonuclease activity, base excision, methylation or other activity that interferes with at least one DNA polymerase activity. Long recognition sequences, comprising infrequently occurring sequence in the sample or comprising underrepresented base combinations (abundance of GC in an AT-rich genome sample or abundance of AT in a GC-rich genome sample) are likely to identify a relatively small number of sites and therefore to direct infrequent nucleic acid modification such as endonuclease activity, base excision, methylation or other activity that interferes with at least one DNA polymerase activity. Accordingly, as disclosed herein, in some embodiments one may regulate the frequency of sequence removal from a sequence reaction through modifications to the length or content of the recognition sequence.

Guide RNA may be synthesized through a number of methods consistent with the disclosure herein. Standard synthesis techniques may be used to produce massive quantities of guide RNAs, and/or for highly-repetitive targeted regions, which may require only a few guide RNA molecules to target a multitude of unwanted loci. The double stranded DNA molecules can comprise an RNA site specific binding sequence, a guide RNA sequence for Cas9 protein and a T7 promoter site. In some cases, the double stranded DNA molecules can be less than about 100 bp length. T7 polymerase can be used to create the single stranded RNA molecules, which may include the target RNA sequence and the guide RNA sequence for the Cas9 protein.

Guide RNA sequences may be designed through a number of methods. For example, in some embodiments, non-genic repeat sequences of the human genome are broken up into, for example, 100 bp sliding windows. Double stranded DNA molecules can be synthesized in parallel on a microarray using photolithography.

The windows may vary in size. 30-mer target sequences can be designed with a short trinucleotide protospacer adjacent motif (PAM) sequence of N-G-G flanking the 5' end of the target design sequence, which in some cases facilitates cleavage. See, among others, Giedrius Gasiunas et al., (2012) "Cas9-crRNA ribonucleoprotein complex mediates specific DNA cleavage for adaptive immunity in bacteria" Proc. Natl. Acad. Sci. USA. September 25, 109(39): E2579-E2586, which is hereby incorporated by reference in its entirety. Redundant sequences can be eliminated and the remaining sequences can be analyzed using a search engine (e.g. BLAST) against the human genome to avoid hybridization against refseq, ENSEMBL and other gene databases to avoid nuclease activity at these sites. The universal Cas9 tracer RNA sequence can be added to the guide RNA target sequence and then flanked by the T7 promoter. The sequences upstream of the T7 promoter site can be synthesized. Due to the highly repetitive nature of the target regions in the human genome, in many embodiments, a relatively small number of guide RNA molecules will digest a larger percentage of NGS library molecules.

Although only about 50% of protein coding genes are estimated to have exons comprising the NGG PAM (photospacer adjacent motif) sequence, multiple strategies are provided herein to increase the percentage of the genome that can be targeted with the Cas9 cutting system. For example, if a PAM sequence is not available in a DNA region, a PAM sequence may be introduced via a combination strategy using a guide RNA coupled with a helper DNA comprising the PAM sequence. The helper DNA can be synthetic and/or single stranded. The PAM sequence in the helper DNA will not be complimentary to the gDNA knockout target in the NGS library, and may therefore be unbound to the target NGS library template, but it can be bound to the guide RNA. The guide RNA can be designed to hybridize to both the target sequence and the helper DNA comprising the PAM sequence to form a hybrid DNA:RNA:DNA complex that can be recognized by the Cas9 system.

The PAM sequence may be represented as a single stranded overhang or a hairpin. The hairpin can, in some cases, comprise modified nucleotides that may optionally be degraded. For example, the hairpin can comprise Uracil, which can be degraded by Uracil DNA Glycosylase.

As an alternative to using a DNA comprising a PAM sequence, modified Cas9 proteins without the need of a PAM sequence or modified Cas9 with lower sensitivity to PAM sequences may be used without the need for a helper DNA sequence.

In further cases, the guide RNA sequence used for Cas9 recognition may be lengthened and inverted at one end to act as a dual cutting system for close cutting at multiple sites. The guide RNA sequence can produce two cuts on a NGS DNA library target. This can be achieved by designing a single guide RNA to alternate strands within a restricted distance. One end of the guide RNA may bind to the forward strand of a double stranded DNA library and the other may bind to the reverse strand. Each end of the guide RNA can comprise the PAM sequence and a Cas9 binding domain. This may result in a dual double stranded cut of the NGS library molecules from the same DNA sequence at a defined distance apart.

The DNA digestion by Cas9 may be performed before or after NGS library generation. The Cas9 protein can be added to the DNA (e.g. NGS library molecules) in vitro (i.e. outside of a cell).

For example, NGS libraries can be introduced to a pool of guide RNAs and a Cas9 protein. Double stranded breaks can occur upstream of the PAM sequences in the target specific domain of the guide RNA. This process in effect cuts the target NGS library molecules in half, rendering the templates unusable for downstream PCR processes that are common in NGS library prep. In this process, genomic DNA can be amplified by a strand displacing polymerase using a random primer with a 5' adapter sequence. During primer extension, biotinylated ddNTPs can be incorporated, which may terminate the copied strand, wherein the ratio of ddNTP to native NTP can be used to determine the average strand length. The copied DNA molecules comprising the adaptor tails can be isolated on a solid support (e.g. streptavidin coated magnetic bead). A second random priming reaction can be initiated with a primer comprising a second 5' adapter sequence.

The most distal random primer extension reaction can displace those primers that bound downstream so that only a single molecule is hydrogen bound to the streptavidin bead that consists of both A and B sequencing adapters. The beads can be washed to remove excess enzyme, NTPs primers and/or short library molecules that were displaced in the second primer extension reaction. The pool of guide RNAs and Cas9 protein complex can be introduced to cut all unwanted library molecules. The remaining un-cut library molecules can be PCR amplified to incorporate the full length sequencing adapters. The adapter sequences can be used for this PCR reaction, so that only molecules with both adapter sequences may amplify. The library molecules that were cut by the RNA guided Cas9 system will not contain both adapter sequences on an intact library molecule and may thus be reduced to background in the final library.

This may result in a sequencing library with dramatically reduced complexity. Unwanted sequences are removed and the remaining sequences can be more readily analyzed by NGS techniques. The reduced complexity of the library can reduce the sequencer capacity required for clinical depth sequencing and/or reduce the computational requirement for accurate mapping of non-repetitive sequences.

Alternative versions of the assay comprise at least one sequence-specific nuclease, and in some cases a combination of sequence-specific nucleases, such as at least one restriction endonuclease having a recognition site that is abundant in a nontarget repeat region. In some cases an enzyme comprises an activity that yields double-stranded breaks in response to a specific sequence. In some cases an enzyme comprises any nuclease or other enzyme that digests double-stranded nucleic acid material in RNA/DNA hybrids.

In addition, in some embodiments at least one target-specific oligo that inhibits PCR is used to block the additional library preparation steps such as PCR amplification with the same result as removing them from the downstream processing steps. For example, synthetic DNA oligos can be produced that allow for crosslinking of single-stranded DNA oligonucleotides that would not denature during PCR or other amplification strategies. Some examples comprise Psoralen crosslinking of synthetic DNA sequences as hybridization probes. Other examples comprise the use of PNAs or locked nucleic acids in the synthetic oligos to block amplification.

Nucleic acid probes (e.g. biotinylated probes) complementary to bait nucleic acids can be hybridized to nucleic acids in solution and pulled down with, e.g., magnetic streptavidin-coated beads. Non bound nucleic acids can be washed away and the captured nucleic acids may then be eluted and amplified for sequencing or genotyping. The methods provided above can be used to reduce the complexity of the bound nucleic acids by cleaving, for example, bound nucleic acids with unwanted regions, e.g. repetitive regions.

In some embodiments, practice of the methods herein reduces the sequencing time duration of a sequencing reaction, such that a nucleic acid library is sequenced in a shorter time, or using fewer reagents, or using less computing power. In some embodiments, practice of the methods herein reduces the sequencing time duration of a sequencing reaction for a given nucleic acid library to about 90%, 80%, 70%, 60%, 50%, 40%, 33%, 30% or less than 30% of the time required to sequence the library in the absence of the practice of the methods herein.

In some embodiments, a specific read sequence from a specific region is of particular interest in a given sequencing reaction. Measures to allow the rapid identification of such a specific region are beneficial as they may decrease computation time or reagent requirements or both computation time and reagent requirements.

Some embodiments relate to the generation of guide RNA molecules. Guide RNA molecules are in some cases transcribed from DNA templates. A number of RNA polymerases may be used, such as T7 polymerase, RNA PolI, RNA PolII, RNA PolIII, an organellar RNA polymerase, a viral RNA polymerase, or a eubacterial or archaeal polymerase. In some cases the polymerase is T7.

Guide RNA generating templates comprise a promoter, such as a promoter compatible with transcription directed by T7 polymerase, RNA PolI, RNA PolII, RNA PolIII, an organellar RNA polymerase, a viral RNA polymerase, or a eubacterial or archaeal polymerase. In some cases the promoter is a T7 promoter.

Guide RNA templates encode a tag sequence in some cases. A tag sequence binds to a nucleic acid modifying enzyme such as a methylase, base excision enzyme or an endonuclease. In the context of a larger Guide RNA molecule bound to a nontarget site, a tag sequence tethers an enzyme to a nucleic acid nontarget region, directing activity to the nontarget site. An exemplary tethered enzyme is an endonuclease such as Cas9.

In many cases, the tag sequence comprises a stem-loop, such as a partial or total stem-loop structure. The 'stem' of the stem loop structure is encoded by a palindromic sequence in some cases, either complete or interrupted to introduce at least one 'kink' or turn in the stem. The 'loop' of the stem loop structure is not involved in stem base pairing in most cases. Stem loop 'hairpin' structures are depicted in FIGS. 1D-2B.

In some cases, the stem loop is encoded by a tracr sequence, such as a tracr sequence disclosed in references incorporated herein. Some stem loops bind, for example, Cas9 or other endonuclease.

Guide RNA molecules additionally comprise a recognition sequence. The recognition sequence is completely or incompletely reverse-complementary to a nontarget sequence to be eliminated from a nucleic acid library sequence set. As RNA is able to hybridize using base pair combinations (G:U base pairing, for example) that do not occur in DNA-DNA hybrids, the recognition sequence does not need to be an exact reverse complement of the nontarget sequence to bind. In addition, small perturbations from complete base pairing are tolerated in some cases.

In some cases, the pairing is complete over the length of the recognition sequence. In some cases, the pairing is sufficient for the recognition sequence to tether the tag sequence to the vicinity of a nontarget sequence, or to tether the tag sequence bound to an enzyme to the nontarget sequence.

Guide RNA templates comprise a promoter, a tag sequence and a recognition sequence. In some cases the tag sequence precedes the recognition sequence, while in some cases the recognition sequence precedes the tag sequence. In some cases the construct is bounded by a transcription termination sequence. In some cases, a tag sequence and a recognition sequence are separated by a cloning site, such that a recognition sequence can be cloned into and cloned out of a construct comprising a promoter and a template encoding a tag sequence.

Figure 3A:
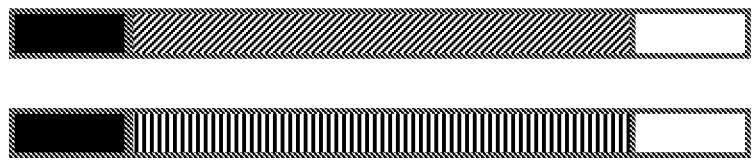
FIG. 3A depicts a sequencing library comprising a first nucleic acid having a nontarget sequence (top, diagonally hashed insert) and a second nucleic acid having a target sequence (bottom, vertically hashed insert).
Figure 3B:
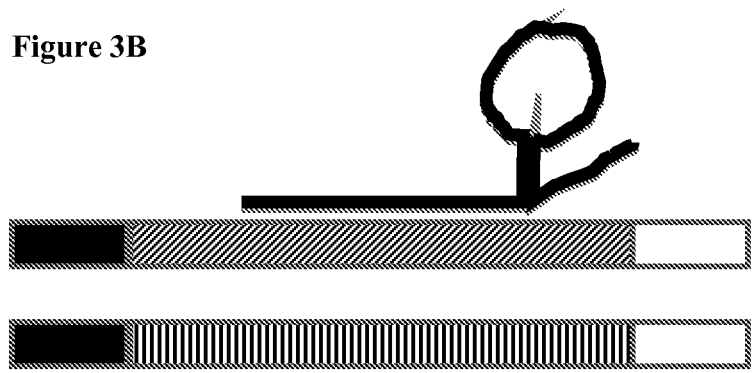
FIG. 3B depicts the nontarget sequence (top, diagonally hashed insert) bound to a guide RNA, while the target sequence (bottom, vertically hashed insert) is unbound.
Figure 3C:
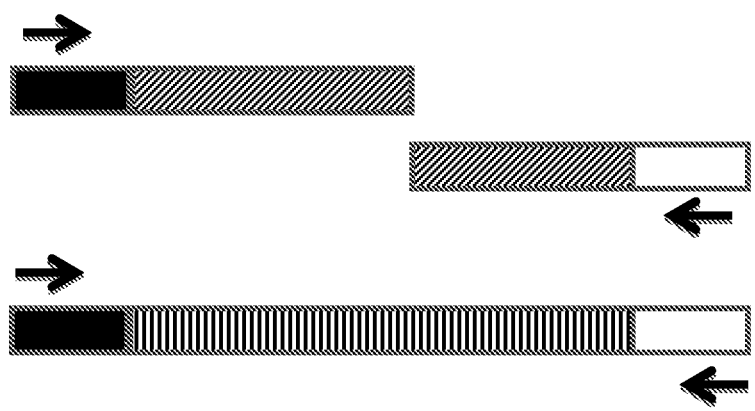
FIG. 3C depicts the results of cleavage of a nontaget molecule. Primers bound to binding sites are indicated as grey arrows. PCR primers have been added, but the nucleic acid comprising the nontarget sequence has been cleaved (top, diagonally hashed insert) such that PCR amplification will not occur. The target nucleic acid molecule (bottom, vertically hashed insert) retains a pair of primer binding sites, and will be amplified.

In FIGS. 3A-3C is seen an embodiment of the present disclosure. In FIG. 3A is seen a library comprising nucleic acids having universal adapter sequences (black, left, and white, right) and comprising target sequence that is either repetitive, 'nontarget sequence' (diagonal hashed box) or nonrepetitive target sequence (vertical striped box). The universal adapter sequences are compatible with a next generation sequencing platform involving sequence by synthesis. In FIG. 3B, a Cas-9 RNA is contacted to the library and binds to the nontarget library sequence. A DNA endonuclease, not shown, identifies the bound Cas-9 structure and is directed to the nontarget sequence, cleaving it. In FIG. 3C, primers (indicated as black arrows, with the arrow point indicating the 3' end of each primer) binding the universal adapters are contacted to the library. The cleaved library molecule comprising nontarget sequence is not able to support polymerase chain reaction amplification because neither half of the cleaved molecule comprises forward and reverse primer binding sites. The library molecule comprising target sequence is able to support polymerase chain reaction amplification because the library molecules comprise a forward (black) and reverse (white) universal adapter region capable of primer binding. In alternative embodiments, the Cas-9 RNA molecule is replaced with an alternative RNA molecule. In alternative embodiments a restriction endonuclease having specificity to a nontarget region is used.

A guide RNA template may be a free molecule or may be cloned in a plasmid, such as a plasmid that directs replication in a cell.

As used herein, "about" a given value is defined as +/−10% of said given value.

As used herein, NGS or Next Generation Sequencing may refer to any number of nucleic acid sequencing technologies, such as 5.1 Massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, Single molecule real time (SMRT) sequencing, Tunneling currents DNA sequencing, Sequencing by hybridization, Sequencing with mass spectrometry, Microfluidic Sanger sequencing, Microscopy-based techniques, RNAP sequencing, and In vitro virus high-throughput sequencing.

As used herein, a 'target sequence' is a sequence of a nucleic acid molecule, alone or in a library. In some cases sequence information is desired for a target sequence. However, in some cases sequence information is desired for a target sequence only if it does not comprise repetitive, information poor, or otherwise undesirable sequence for downstream applications.

As used herein, a 'nontarget sequence' is a sequence of a sequencing library molecule that is to be excluded from a library prior to sequencing or that is to be excluded from sequence data generated from a sequencing reaction. Non-target sequence is a subset of target sequence that is to be excluded from target sequencing for any number of reasons, such as because it comprises repetitive sequence, information poor sequence, or otherwise undesirable sequence for downstream applications.

As used herein, to 'modify' a nucleic acid is to cause a change to a covalent bond in the nucleic acid, such as methylation, base removal, or cleavage of a phosphodiester backbone.

As used herein, to 'direct transcription' is to provide template sequence from which a specified RNA molecule can be transcribed.

EXAMPLES

Example 1

A nucleic acid sequencing library is generated from a nucleic acid sample known to comprise a substantial amount of GC-rich repetitive regions. The library comprises nucleic acid molecules each comprising a first adapter and a second adapter flanking a region of about 100-500 bases of target sequence. The library is bound to a sequencing chip surface through the first adapter and the second adapter of each library member. The bound library molecules are contacted with the restriction endonuclease NotI, which targets palindromic sequences having a '5 end of CGCC. NGS is performed on the treated nucleic acid sequencing library. It is observed that no sequence comprising a 5' CGCC palindromic sequence is included in the sequencing results, although palindromic sequences having 5' CGCC ends are known to be common in the genome of the sample source.

Example 2

A nucleic acid sequencing library is generated from a nucleic acid sample from a human. The library is divided into equal aliquots, each of which comprises target sequence in excess of 1× coverage of the complete genome of the human sample.

A first aliquot contacted with a population of guide RNA-Cas9 complexes. The guide RNA population comprises guide RNA comprising a recognition sequence reverse-complementary to an Alu repeat sequence, as well as guide RNA comprising a recognition sequence reverse complementary to SINE repeats and guide RNA comprising a recognition sequence reverse complementary to LINE repeats. Each guide RNA recognition is linked immediately downstream to a stem-loop tag sequencing that binds a Cas9 endonuclease.

The Cas9 guide RNA complexes bind to their respective Alu, SINE and LINE recognition sequences within the sequencing library and cleave the library molecules harboring recognition sequence.

The treated library is bound to a sequencing chip surface through at least one of the first adapter and the second adapter of each library member. A sequencing reaction is performed and sequence data for the target region of each library molecule having a first and a second adapter is generated.

A second, untreated aliquot is bound to a sequencing chip surface through the first adapter and the second adapter of each library member.

It is observed that the sequencing data generated from the first aliquot does not include Alu, SINE and LINE repeat sequence, while the sequencing data from the second aliquot includes Alu, SINE and LINE repeat sequence. The sequencing data from the first aliquot is about ⅓ the size, requires substantially less computing time to assemble into contigs, and requires substantially fewer reagents than does the second aliquot.

It is observed that the first and second aliquot, despite their difference in total data size, contain substantially the same information aside from the Alu, SINE and LINE sequences. When the Alu, SINE and LINE repeats are computationally removed from the sequence generated from the second aliquot, the remaining data is not substantially different between the first and second aliquots' sequence.

Example 3

A nucleic acid sequencing library is generated from a nucleic acid sample from a human and partitioned into two aliquots, as in Example 2, above. The library in each aliquot is separately bound to a sequencing chip surface through the first adapter and the second adapter of each library member.

Subsequent to binding to the sequencing chips, the first aliquot is contacted with a population of guide RNA-Cas9 complexes. The guide RNA population comprises guide RNA comprising a recognition sequence reverse-complementary to an Alu repeat sequence, as well as guide RNA comprising a recognition sequence reverse complementary to SINE repeats and guide RNA comprising a recognition sequence reverse complementary to LINE repeats. Each guide RNA recognition is linked immediately downstream to a stem-loop sequencing that binds a Cas9 endonuclease.

The Cas9 guide RNA complexes bind to their respective Alu, SINE and LINE recognition sequences within the sequencing library and cleave the library molecules harboring recognition sequence.

As in Example 2, above, it is observed that the sequencing data generated from the first aliquot does not include Alu, SINE and LINE repeat sequence, while the sequencing data from the second aliquot includes Alu, SINE and LINE repeat sequence. The sequencing data from the first aliquot is about ⅓ the size, requires substantially less computing time to assemble into contigs, and requires substantially fewer reagents than does the second aliquot.

It is observed that the first and second aliquot, despite their difference in total data size, contain substantially the same information aside from the Alu, SINE and LINE sequences. When the Alu, SINE and LINE repeats are computationally removed from the sequence generated from the second aliquot, the remaining data is not substantially different between the first and second aliquots' sequence.

Example 4

A nucleic acid sequencing library is generated from an RNA sample from a human patient. Total RNA is extracted and reverse-transcribed to generate cDNA, and adapters are added to the 5' and 3' ends of the cDNA generated.

The library is separated into aliquots, each of which representing greater than 1× coverage of the transcriptome.

A first and a second aliquot of the library are separately bound to a sequencing chip surface through the first adapter and the second adapter of each library member.

Subsequent to binding to the sequencing chips, the first aliquot contacted with a population of guide RNA-Cas9 complexes. The guide RNA population comprises guide RNA comprising a recognition sequence reverse-complementary to large subunit 5S ribosomal RNA sequence, 5.8S ribosomal RNA sequence, and 28S ribosomal RNA sequence, and to small subunit 18S ribosomal RNA sequence.

Each guide RNA recognition is linked immediately downstream to a stem-loop sequencing that binds a Cas9 endonuclease.

The Cas9 guide RNA complexes bind to their respective ribosomal RNA recognition sequences within the sequencing library and cleave the library molecules harboring recognition sequence.

As in Example 2, above, it is observed that the sequencing data generated from the first aliquot does not include 'non-target' ribosomal RNA sequence bound by the guide RNA, while the sequencing data from the second aliquot includes 5S, 5.8S, 28S and 18S sequence. The sequencing data from the first aliquot is about 1/10 the size, requires substantially less computing time to assemble into contigs, and requires substantially fewer reagents than does the second aliquot.

It is observed that the first and second aliquot, despite their difference in total data size, contain substantially the same information aside from the 5S, 5.8S, 28S and 18S sequences. When the 5S, 5.8S, 28S and 18S sequence are computationally removed from the sequence generated from the second aliquot, the remaining data is not substantially different between the first and second aliquots' sequence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of excluding an exclusion sequence from a nucleic acid library sequence dataset comprising:
   (a) providing a double stranded nucleic acid library, comprising a plurality of double stranded nucleic acid molecules, wherein each double stranded nucleic acid molecule comprises a first adapter region, a target sequence, and a second adapter region, and wherein at least one of said double stranded nucleic acid molecules comprises said exclusion sequence;
   (b) contacting the double stranded nucleic acid library to a nucleic acid modifying moiety comprising a guide RNA molecule that binds with said exclusion sequence; and
   (c) sequencing said double stranded nucleic acid library using a sequencing approach that requires said first adapter region and said second adapter region spanning said target sequence;

thereby generating said nucleic acid library sequence dataset comprising said target sequence and not comprising said exclusion sequence;
wherein said contacting comprises cleaving said exclusion sequence.

2. The method of claim 1, wherein said sequencing comprises next-generation sequencing.

3. The method of claim 1, wherein said sequencing comprises amplifying said target sequence using a first primer that anneals to said first adaptor region and a second primer that anneals to said second adaptor region.

4. The method of claim 1, wherein said contacting interferes with said sequencing.

5. The method of claim 1, wherein said contacting comprises cleaving said exclusion sequence such that said first adapter region and said second adapter region are not physically joined through said target sequence comprising said exclusion sequence.

6. The method of claim 1, wherein said nucleic acid modifying moiety comprises an enzyme having base excision activity.

7. The method of claim 1, wherein said nucleic acid modifying moiety comprises the guide RNA molecule comprising a protospacer adjacent motif sequence.

8. The method of claim 1, wherein said nucleic acid modifying moiety comprises a guide RNA molecule-directed endonuclease.

9. The method of claim 8, wherein said guide RNA molecule-directed endonuclease comprises a Cas9 endonuclease.

10. The method of claim 1, wherein said exclusion sequence comprises low-information content sequence.

11. The method of claim 1, wherein said exclusion sequence comprises DNA encoding ribosomal RNA.

12. The method of claim 1, wherein said exclusion sequence comprises a repetitive sequence, an Alu repeat sequence, a SINE element sequence, LINE sequence, DNA encoding ribosomal RNA, telomeric sequence, subtelomeric sequence, centromeric sequence, a single repeat, or combinations thereof.

13. The method claim 1, wherein said exclusion sequence comprises at least 10% of said nucleic acid library target sequence.

14. The method of claim 1, wherein at least one nucleic acid of said library is bound to a next generation sequencing platform.

15. The method of claim 14, wherein said next generation sequencing platform comprises at least one of a solid platform, a bead, a lipid or oil droplet, and a well surface.

16. The method of claim 1, wherein the method results in a sequencing library having reduced complexity.

17. The method of claim 1, wherein the cleaving creates double stranded breaks in the exclusion nucleic acid sequence.

* * * * *